US010211484B2

(12) United States Patent
Schmitz et al.

(10) Patent No.: US 10,211,484 B2
(45) Date of Patent: Feb. 19, 2019

(54) ACETIC ACID 2-[(METHOXYCARBONYL)OXY] METHYL ESTER AS ELECTROLYTE COMPONENT

(71) Applicant: Gotion, Inc., Fremont, CA (US)

(72) Inventors: Rene Schmitz, Stuttgart (DE); Karolin Geyer, Ludwigshafen (DE)

(73) Assignee: Gotion Inc., Fremont, CA (US)

( * ) Notice: Subject to any disclaimer, the term of this patent is extended or adjusted under 35 U.S.C. 154(b) by 0 days.

(21) Appl. No.: 15/526,601

(22) PCT Filed: Nov. 3, 2015

(86) PCT No.: PCT/EP2015/075555
§ 371 (c)(1),
(2) Date: May 12, 2017

(87) PCT Pub. No.: WO2016/074987
PCT Pub. Date: May 19, 2016

(65) Prior Publication Data
US 2017/0338523 A1    Nov. 23, 2017

(30) Foreign Application Priority Data

Nov. 13, 2014  (EP) .................................. 14192987

(51) Int. Cl.
| | |
|---|---|
| *H01M 10/0567* | (2010.01) |
| *H01M 10/0568* | (2010.01) |
| *H01M 10/0569* | (2010.01) |
| *H01M 10/0525* | (2010.01) |
| *H01M 10/42* | (2006.01) |
| *H01M 4/133* | (2010.01) |
| *H01M 10/052* | (2010.01) |
| *C07C 69/96* | (2006.01) |
| *H01M 4/587* | (2010.01) |

(52) U.S. Cl.
CPC ......... *H01M 10/4235* (2013.01); *C07C 69/96* (2013.01); *H01M 4/133* (2013.01); *H01M 4/587* (2013.01); *H01M 10/052* (2013.01); *H01M 10/0525* (2013.01); *H01M 10/0567* (2013.01); *H01M 10/0568* (2013.01); *H01M 10/0569* (2013.01); *H01M 2300/0017* (2013.01); *H01M 2300/0037* (2013.01)

(58) Field of Classification Search
CPC ......... H01M 10/0567; H01M 10/0568; H01M 10/0569; H01M 10/4235; H01M 2300/0037; H01M 10/052; H01M 10/0525; H01M 2300/0017
See application file for complete search history.

(56) References Cited

U.S. PATENT DOCUMENTS

| | | | |
|---|---|---|---|
| 6,455,200 B1 * | 9/2002 | Prakash ............ | H01M 10/0525 429/203 |
| 2010/0304225 A1 | 12/2010 | Pascaly et al. | |
| 2012/0171581 A1 | 7/2012 | Abe et al. | |

FOREIGN PATENT DOCUMENTS

| | | |
|---|---|---|
| EP | 2 023 434 A1 | 2/2009 |
| EP | 2 479 831 A1 | 7/2012 |
| WO | WO 2013/026854 A1 | 2/2013 |

OTHER PUBLICATIONS

Extended European Search Report dated May 26, 2015 in European Patent Application No. 14192987.7.
International Preliminary Report on Patentability and Written Opinion dated May 26, 2017 in PCT/EP2015/075555.
International Search Report and Written Opinion dated Jan. 19, 2016 in PCT/EP2015/075555.
U.S. Appl. No. 14/188,895, filed Feb. 25, 2014, Jurgen Wortmann, et al.
U.S. Appl. No. 15/030,973, filed Apr. 21, 2016, Nicole Holub, et al.
U.S. Appl. No. 15/121,613, filed Aug. 25, 2016, Arnd Garsuch, et al.
U.S. Appl. No. 15/301,005, filed Sep. 30, 2016, Arnd Garsuch, et al.
U.S. Appl. No. 15/304,255, filed Oct. 14, 2016, Rene Schmitz, et al.
U.S. Appl. No. 15/304,726, filed Oct. 17, 2016, Rene Schmitz, et al.
U.S. Appl. No. 15/129,658, filed Sep. 27, 2016, Rene Schmitz, et al.
U.S. Appl. No. 15/326,883, filed Jan. 17, 2017, Rene Schmitz, et al.

* cited by examiner

*Primary Examiner* — Anca Eoff
(74) *Attorney, Agent, or Firm* — Young Basile Hanlon & MacFarlane, P.C.

(57) ABSTRACT

An electrolyte composition containing (i) at least one aprotic organic solvent; (ii) at least one conducting salt; (iii) acetic acid 2-[(methoxycarbonyl)oxy] methyl ester; and (vi) optionally one or more additives.

10 Claims, No Drawings

ACETIC ACID 2-[(METHOXYCARBONYL)OXY] METHYL ESTER AS ELECTROLYTE COMPONENT

The present invention relates to an electrolyte composition containing acetic acid 2-[(methoxycarbonyl)oxy] methyl ester, to its use as additive in electrolyte compositions for electrochemical cells and to electrochemical cells comprising such electrolyte composition.

Storing electrical energy is a subject of still growing interest. Efficient storage of electric energy would allow electric energy to be generated when it is advantageous and used when needed. Secondary electrochemical cells are well suited for this purpose due to their rechargeability. Secondary lithium batteries are of special interest for energy storage since they provide high energy density due to the small atomic weight and the large ionization energy of lithium and have become widely used as a power source for many portable electronics such as cellular phones, laptop computers, mini-cameras, etc.

In secondary lithium batteries like lithium ion batteries organic carbonates, ethers, esters and ionic liquids are used as sufficiently polar solvents. Most state of the art lithium ion batteries in general comprise not a single solvent but a solvent mixture of different organic aprotic solvents. Very common combinations of solvents are mixtures of cyclic organic carbonates and acyclic organic carbonates. Cyclic carbonates have high dielectric constants providing high solubility of the conductive salts used in electrolyte compositions. Acyclic carbonates have comparatively low viscosity and are added to the electrolyte compositions to reduce the viscosity and depending on the other components to reduce the melting point of the electrolyte compositions. The most common cyclic carbonates are ethylene carbonate and propylene carbonate. Ethylene carbonate has a melting point of about +36° C., so its application in low temperature applications is limited. Ethylene carbonate can only be used in compositions containing comparably large amounts of low molecular organic solvents like acyclic carbonates. Large amounts of acyclic carbonates may be undesirable due to their comparatively high flammability. Propylene carbonate has a melting point of about −45° C., which is desirable for low temperature applications but is difficult to use in combination with graphite which is a common anode active material in secondary lithium ion batteries. Propylene carbonate intercalates into the graphite used as anode active material thereby destroying the graphite by exfoliation.

During charge and discharge of lithium ion batteries various reactions take place at different cell potentials. It is known that during the first charging process of a lithium ion battery usually a film is formed on the anode. This film is often called solid electrolyte interface (SEI). The SEI is permeable for lithium ions and protects the electrolyte composition from direct contact with the anode and vice versa. It is formed by reductive decomposition of components of the electrolyte composition like solvents, e.g. carbonates, esters, and ethers, and conductive salts on the surface of the anode, especially if the anode active material is a carbonaceous material like graphite. A certain amount of the lithium of the cathode is irreversibly consumed for the formation of the SEI and cannot be replaced. Structure and properties of the SEI may be significantly influenced by addition of suitable chemical compounds which are easily decomposed on the anode by reduction and thereby forming a film on the surface of the anode. This is also a possibility to reduce the amount of irreversibly consumed lithium. The SEI has a significant influence on cycling stability, calendar ageing, and durability (high-current resistance) of an electrochemical or electrooptical device. An example of a well-known SEI forming additive is vinylene carbonate. Nevertheless, there is still the need for further SEI-forming additives to broaden their application range. For example, despite the fact that a large number of SEI additives is known until now, the use of propylene carbonate in electrochemical cells comprising graphite as anode active material is still difficult due to its intercalation into the graphite structure and the destruction of the graphite structure by this intercalation.

It is the object of the present invention to provide electrolyte compositions with long cycle life. It is another object of the present invention to provide electrolyte compositions which can be used in a wide temperature range, in particular electrolyte compositions applicable at low temperatures. It is another object of the present invention to provide electrolyte compositions which can be used at low temperatures and have a low flammability. It is a further object of the present invention to provide electrolyte compositions containing propylene carbonate, which are suited for use in secondary lithium batteries with long cycle life and to provide secondary lithium batteries comprising carbonaceous materials which are susceptible to deterioration by propylene carbonate as anode active material and an electrolyte composition containing propylene carbonate.

This object is achieved by an electrolyte composition containing
(i) at least one aprotic organic solvent;
(ii) at least one conducting salt;
(iii) acetic acid 2-[(methoxycarbonyl)oxy] methyl ester; and
(vi) optionally one or more additives.

The problem is further solved by the use of acetic acid 2-[(methoxycarbonyl)oxy] methyl ester as additive in electrolyte compositions, and by electrochemical cells comprising the electrolyte composition.

Electrochemical cells comprising electrolyte compositions containing acetic acid 2-[(methoxycarbonyl)oxy] methyl ester show good cycling performance. Acetic acid 2-[(methoxycarbonyl)oxy] methyl ester is so effective that even electrolyte compositions containing large amounts of propylene carbonate can be used in secondary lithium batteries comprising a graphite anode. The use of acetic acid 2-[(methoxycarbonyl)oxy] methyl ester as additive allows the provision of electrolyte compositions comprising propylene carbonate. Such electrolyte compositions have low melting points and can be used at low temperatures. The flashpoints of such propylene carbonate containing electrolytes are comparable to ethylene carbonate containing electrolyte compositions.

In the following the invention is described in detail.

The electrolyte composition according to the present invention contains
(i) at least one aprotic organic solvent;
(ii) at least one conducting salt;
(iii) acetic acid 2-[(methoxycarbonyl)oxy] methyl ester; and
(vi) optionally one or more additives.

The electrolyte composition preferably contains at least one aprotic organic solvent as component (i), more preferred at least two aprotic organic solvents (i). According to one embodiment the electrolyte composition may contain up to ten aprotic organic solvents.

The at least one aprotic organic solvent (i) is preferably selected from cyclic and acyclic organic carbonates, di-$C_1$-$C_{10}$-alkylethers, di-$C_1$-$C_4$-alkyl-$C_2$-$C_6$-alkylene ethers and polyethers, cyclic ethers, cyclic and acyclic acetales and ketales, orthocarboxylic acids esters, cyclic and acyclic esters of carboxylic acids, cyclic and acyclic sulfones, and cyclic and acyclic nitriles and dinitriles.

More preferred the at least one aprotic organic solvent (i) is selected from cyclic and acyclic organic carbonates, di-$C_1$-$C_{10}$-alkylethers, di-$C_1$-$C_4$-alkyl-$C_2$-$C_6$-alkylene ethers and polyethers, cyclic and acyclic acetales and ketales, and cyclic and acyclic esters of carboxylic acids, even more preferred the at least one aprotic organic solvent (i) is selected from cyclic and acyclic organic carbonates and cyclic and acyclic esters of carboxylic acids, and most preferred the at least one aprotic organic solvent (i) is selected from cyclic and acyclic organic carbonates. It is in particular preferred that the electrolyte composition contains at least one aprotic organic solvent (i) comprising at least one cyclic organic carbonate, it is especially preferred that the electrolyte composition contains at least one aprotic organic solvent (i) comprising propylene carbonate.

According to one embodiment the at least one aprotic organic solvent (i) comprises at least one acyclic organic carbonate and at least one cyclic organic carbonate, preferably at least one acyclic organic carbonate and propylene carbonate. If the at least one aprotic organic solvent (i) comprises at least one acyclic organic carbonate and at least one cyclic organic carbonate the ratio by weight of acyclic organic carbonates to cyclic organic carbonates is preferably in the range of from 1:10 to 10:1, more preferred in the range of from 4:1 to 1:4.

According to another embodiment the at least one aprotic organic solvent (i) comprises at least one cyclic organic carbonate and at least one acyclic ester of carboxylic acids, preferably at least one alkylester of carboxylic acids and propylene carbonate. If the at least one aprotic organic solvent (i) comprises at least one alkyl ester of carboxylic acids and at least one cyclic organic carbonate the ratio by weight of alkyl ester of carboxylic acids to cyclic organic carbonates is preferably in the range of from 1:10 to 10:1, more preferred in the range of from 4:1 to 1:4. The alkyl ester of carboxylic acids are preferably selected from esters of $C_1$-$C_4$ alcohols with $C_1$-$C_4$ carboxylic acids, for example esters of methanol, ethanol, i-propanol or n-propanol with formic acid, acetic acid or propionic acid like methyl formiate, ethyl formiate, i- and n-propyl formiate, methyl acetate, ethyl acetate, i- and n-propyl acetate, methyl propionate, ethyl propionate, and i- and n-propyl propionate.

In case the at least one aprotic solvent (i) comprises propylene carbonate, it is preferred if the concentration of the propylene carbonate is at least 10 wt.-%, more preferred at least 20 wt.-%, even more preferred at least 30 wt.-%, and most preferred at least 40 wt.-%, based on the total weight of the electrolyte composition.

The aprotic organic solvents may be partly halogenated, e.g. they may be partly fluorinated, partly chlorinated or partly brominated, and preferably they may be partly fluorinated. "Partly halogenated" means, that one or more H of the respective molecule is substituted by a halogen atom, e.g. by F, Cl or Br. Preference is given to the substitution by F. The at least one solvent may be selected from partly halogenated and non-halogenated aprotic organic solvents, i.e. the electrolyte composition may contain a mixture of partly halogenated and non-halogenated aprotic organic solvents.

Examples of cyclic organic carbonates are ethylene carbonate (EC), propylene carbonate (PC) and butylene carbonate (BC), wherein one or more H of the alkylene chain may be substituted by F and/or an $C_1$ to $C_4$ alkyl group, e.g. 4-methyl ethylene carbonate, monofluoroethylene carbonate (FEC), and cis- and trans-difluoroethylene carbonate. Preferred cyclic organic carbonates are ethylene carbonate, monofluoroethylene carbonate and propylene carbonate, in particular ethylene carbonate and propylene carbonate.

Examples of acyclic organic carbonates are di-$C_1$-$C_{10}$-alkylcarbonates, wherein each alkyl group is selected independently from each other, preferred are di-$C_1$-$C_4$-alkylcarbonates. Examples are e.g. diethyl carbonate (DEC), ethyl methyl carbonate (EMC), dimethyl carbonate (DMC), and methylpropyl carbonate. Preferred acyclic organic carbonates are diethyl carbonate (DEC), ethyl methyl carbonate (EMC), and dimethyl carbonate (DMC).

According to the invention each alkyl group of the di-$C_1$-$C_{10}$-alkylethers is selected independently from the other. Examples of di-$C_1$-$C_{10}$-alkylethers are dimethylether, ethylmethylether, diethylether, methylpropylether, diisopropylether, and di-n-butylether.

Examples of di-$C_1$-$C_4$-alkyl-$C_2$-$C_6$-alkylene ethers are 1,2-dimethoxyethane, 1,2-diethoxyethane, diglyme (diethylene glycol dimethyl ether), triglyme (triethyleneglycol dimethyl ether), tetraglyme (tetraethyleneglycol dimethyl ether), and diethylenglycoldiethylether.

Examples of suitable polyethers are polyalkylene glycols, preferably poly-$C_1$-$C_4$-alkylene glycols and especially polyethylene glycols. Polyethylene glycols may comprise up to 20 mol % of one or more $C_1$-$C_4$-alkylene glycols in copolymerized form. Polyalkylene glycols are preferably dimethyl- or diethyl-end-capped polyalkylene glycols. The molecular weight $M_w$ of suitable polyalkylene glycols and especially of suitable polyethylene glycols may be at least 400 g/mol. The molecular weight $M_w$ of suitable polyalkylene glycols and especially of suitable polyethylene glycols may be up to 5 000 000 g/mol, preferably up to 2 000 000 g/mol.

Examples of cyclic ethers are 1,4-dioxane, tetrahydrofuran, and their derivatives like 2-methyl tetrahydrofuran.

Examples of acyclic acetals are 1,1-dimethoxymethane and 1,1-diethoxymethane. Examples of cyclic acetals are 1,3-dioxane, 1,3-dioxolane, and their derivatives such as methyl dioxolane.

Examples of acyclic orthocarboxylic acid esters are tri-$C_1$-$C_4$ alkoxy methane, in particular trimethoxymethane and triethoxymethane. Examples of suitable cyclic orthocarboxylic acid esters are 1,4-dimethyl-3,5,8-trioxabicyclo[2.2.2]octane and 4-ethyl-1-methyl-3,5,8-trioxabicyclo[2.2.2]octane.

Examples of acyclic esters of carboxylic acids are ethyl and methyl formiate, ethyl and methyl acetate, ethyl and methyl proprionate, and ethyl and methyl butanoate, and esters of dicarboxylic acids like 1,3-dimethyl propanedioate. An example of a cyclic ester of carboxylic acids (lactones) is γ-butyrolactone.

Examples of cyclic and acyclic sulfones are ethyl methyl sulfone, dimethyl sulfone, and tetrahydrothiophene-S,S-dioxide (sulfolane).

Examples of cyclic and acyclic nitriles and dinitriles are adipodinitrile, acetonitrile, propionitrile, and butyronitrile.

The inventive electrolyte composition contains at least one conducting salt (ii). The electrolyte composition functions as a medium that transfers ions participating in the electrochemical reaction taking place in an electrochemical cell. The conducting salt(s) (ii) present in the electrolyte are usually solvated in the aprotic organic solvent(s) (i). Preferably the conducting salt is a lithium salt.

The conducting salt is preferably selected from the group consisting of

Li[F$_{6-x}$P(C$_y$F$_{2y+1}$)$_x$], wherein x is an integer in the range from 0 to 6 and y is an integer in the range from 1 to 20;

Li[B(R$^I$)4], Li[B(R$^I$)2(OR$^{II}$O)] and Li[B(OR$^{II}$O)2] wherein each R$^I$ is independently from each other selected from F, Cl, Br, I, C1-C4 alkyl, C2-C4 alkenyl, C2-C4 alkynyl, OC1-C4 alkyl, OC2-C4 alkenyl, and OC2-C4 alkynyl wherein alkyl, alkenyl, and alkynyl may be substituted by one or more OR$^{III}$, wherein R$^{III}$ is selected from C1-C6 alkyl, C2-C6 alkenyl, and C2-C6 alkynyl, and (OR$^{II}$O) is a bivalent group derived from a 1,2- or 1,3-diol, a 1,2- or 1,3-dicarboxylic acid or a 1,2- or 1,3-hydroxycarboxylic acid, wherein the bivalent group forms a 5- or 6-membered cycle via the both oxygen atoms with the central B-atom;

LiClO$_4$; LiAsF$_6$; LiCF$_3$SO$_3$; Li$_2$SiF$_6$; LiSbF$_6$; LiAlCl$_4$, Li(N(SO$_2$F)$_2$), lithium tetrafluoro (oxalato) phosphate; lithium oxalate; and salts of the general formula Li[Z(C$_n$F$_{2n+1}$SO$_2$)$_m$], where m and n are defined as follows:

m=1 when Z is selected from oxygen and sulfur,
m=2 when Z is selected from nitrogen and phosphorus,
m=3 when Z is selected from carbon and silicon, and
n is an integer in the range from 1 to 20.

Suited 1,2- and 1,3-diols from which the bivalent group (OR$^{II}$O) is derived may be aliphatic or aromatic and may be selected, e.g., from 1,2-dihydroxybenzene, propane-1,2-diol, butane-1,2-diol, propane-1,3-diol, butan-1,3-diol, cyclohexyl-trans-1,2-diol and naphthalene-2,3-diol which are optionally are substituted by one or more F and/or by at least one straight or branched non fluorinated, partly fluorinated or fully fluorinated C$_1$-C$_4$ alkyl group. An example for such 1,2- or 1,3-diole is 1,1,2,2-tetra(trifluoromethyl)-1,2-ethane diol.

"Fully fluorinated C$_1$-C$_4$ alkyl group" means, that all H-atoms of the alkyl group are substituted by F.

Suited 1,2- or 1,3-dicarboxylic acids from which the bivalent group (OR$^{II}$O) is derived may be aliphatic or aromatic, for example oxalic acid, malonic acid (propane-1,3-dicarboxylic acid), phthalic acid or isophthalic acid, preferred is oxalic acid. The 1,2- or 1,3-dicarboxylic acids are optionally substituted by one or more F and/or by at least one straight or branched non fluorinated, partly fluorinated or fully fluorinated C$_1$-C$_4$ alkyl group.

Suited 1,2- or 1,3-hydroxycarboxylic acids from which the bivalent group (OR$^{II}$O) is derived may be aliphatic or aromatic, for example salicylic acid, tetrahydro salicylic acid, malic acid, and 2-hydroxy acetic acid, which are optionally substituted by one or more F and/or by at least one straight or branched non fluorinated, partly fluorinated or fully fluorinated C$_1$-C$_4$ alkyl group. An example for such 1,2- or 1,3-hydroxycarboxylic acids is 2,2-bis(trifluoromethyl)-2-hydroxy-acetic acid.

Examples of Li[B(R$^I$)$_4$], Li[B(R$^I$)$_2$(OR$^{II}$O)] and Li[B(OR$^{II}$O)$_2$] are LiBF$_4$, lithium difluoro oxalato borate and lithium dioxalato borate.

Preferably the at least one conducting salt is selected from LiPF$_6$, LiBF$_4$, and LiPF$_3$(CF$_2$CF$_3$)$_3$, more preferred the conducting salt is selected from LiPF$_6$ and LiBF$_4$, and the most preferred conducting salt is LiPF$_6$.

The at least one conducting salt is usually present at a minimum concentration of at least 0.1 m/l, preferably the concentration of the at least one conducting salt is 0.5 to 2 mol/l based on the entire electrolyte composition.

The electrolyte composition of the present invention contains acetic acid 2-[(methoxycarbonyl)oxy] methyl ester as component (iii) which has the chemical formula (I)

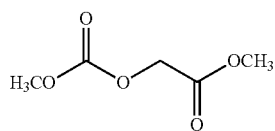

(I)

The concentration of the acetic acid 2-[(methoxycarbonyl)oxy] methyl ester in the electrolyte composition according to the present invention is usually at least 0.05 wt.-%, preferably the concentration is in the range of 0.1 to 10 wt.-%, more preferred in the range of 0.5 to 2 wt.-%, based on the total weight of the electrolyte composition.

Acetic acid 2-[(methoxycarbonyl)oxy] methyl ester may be prepared by reaction of glycolacidmethylester with methylchloroformiate in the presence of a base catalyst.

A further object of the present invention is the use of acetic acid 2-[(methoxycarbonyl)oxy] methyl ester as additive in electrolyte compositions, preferably as film forming additive in electrolyte compositions. It is in particular advantageous to use acetic acid 2-[(methoxycarbonyl)oxy] methyl ester as additive in electrolyte compositions containing propylene carbonate, and especially beneficial is the use acetic acid 2-[(methoxycarbonyl)oxy] methyl ester as additive in electrolyte compositions containing propylene carbonate for use in lithium batteries comprising an anode active material selected from carbonaceous materials prone to deterioration by propylene carbonate.

Acetic acid 2-[(methoxycarbonyl)oxy] methyl ester is usually used by adding the desired amount to the electrolyte composition. Acetic acid 2-[(methoxycarbonyl)oxy] methyl ester is usually used in the electrolyte composition in a concentration of at least 0.05 wt.-%, preferably in the concentration range of 0.1 to 10 wt.-%, more preferred in the concentration range of 0.5 to 2 wt.-%, based on the total weight of the electrolyte composition.

The electrolyte composition according to the present invention may contain at least one further additive (iv). The additive(s) (iv) may be selected from SEI forming additives, flame retardants, overcharge protection additives, wetting agents, HF and/or H$_2$O scavenger, stabilizer for LiPF$_6$ salt, ionic salvation enhancer, corrosion inhibitors, gelling agents, and the like.

The one or more additives (iv) are different from acetic acid 2-[(methoxycarbonyl)oxy] methyl ester.

Examples of flame retardants are organic phosphorous compounds like cyclophosphazenes, organic phosphoramides, organic phosphites, organic phosphates, organic phosphonates, organic phosphines, and organic phosphinates, and fluorinated derivatives thereof.

Examples of cyclophosphazenes are ethoxypentafluorocyclotriphosphazene, available under the trademark Phoslyte™ E from Nippon Chemical Industrial, hexamethylcyclotriphosphazene, and hexamethoxycyclotriphosphazene, preferred is ethoxypentafluorocyclotriphosphazene. An example of an organic phosphoramide is hexamethyl phosphoramide. An example of an organic phosphite is tris(2,2,2-trifluoroethyl) phospite. Examples of organic phosphates are trimethyl phosphate, trimethyl phosphate, tris(2,2,2-trifluoroethyl)phosphate, bis(2,2,2-trifluoroethyl) methyl phosphate, and triphenyl phosphate Examples of organic phosphonates are dimethyl phosphonate, ethyl methyl phosphonate, methyl n-propyl phosphonate, n-butyl methyl phosphonate, diethyl phosphonate, ethyl n-propyl phosphonate, ethyl n-butyl phosphonate, di-n-propyl phosphonate, n-butyl n-propyl phosphonate, di-n-butyl phosphonate, and bis(2,2,2-trifluoroethyl) methyl phosphonate. An example of an organic phosphine is triphenyl phosphine. Examples of organic phosphinates are dimethyl phosphonate, diethyl phosphinate, di-n-propyl phosphinate, trimethyl phosphinate, trimethyl phosphinate, and tri-n-propyl phosphinate.

Examples of HF and/or $H_2O$ scavenger are optionally halogenated cyclic and acyclic silylamines.

A SEI forming additive according to the present invention is a compound which decomposes on an electrode to form a passivation layer on the electrode which prevents degradation of the electrolyte and/or the electrode. In this way, the lifetime of a battery is significantly extended. The term "SEI" means "solid electrolyte interface". SEI forming additives are also named film forming additives and the two terms are used interchangeably herein. Preferably the SEI forming additive forms a passivation layer on the anode. An anode in the context of the present invention is understood as the negative electrode of a battery. Preferably, the anode has a reduction potential of 1 Volt or less against lithium such as a lithium intercalating graphite anode. In order to determine if a compound qualifies as anode film forming additive, an electrochemical cell can be prepared comprising a graphite electrode and a lithium-ion containing cathode, for example lithium cobalt oxide, and an electrolyte containing a small amount of said compound, typically from 0.1 to 10 wt.-% of the electrolyte composition, preferably from 0.2 to 5 wt.-% of the electrolyte composition. Upon application of a voltage between anode and cathode, the differential capacity of the electrochemical cell is recorded between 0.5 V and 2 V vs. a Lithium metal reference. If a significant differential capacity is observed during the first cycle, for example −150 mAh/V at 1 V, but not or essentially not during any of the following cycles in said voltage range, the compound can be regarded as SEI forming additive. SEI forming additives per se are known to the person skilled in the art.

Examples of SEI forming additives are vinylene carbonate and its derivatives such as vinylene carbonate and methylvinylene carbonate; fluorinated ethylene carbonate and its derivatives such as monofluoroethylene carbonate, cis- and trans-difluorocarbonate; propane sultone and its derivatives; ethylene sulfite and its derivatives; oxalate comprising compounds such as lithium oxalate, oxalato borates including dimethyl oxalate, lithium bis(oxalate) borate, lithium difluoro (oxalato) borate, and ammonium bis(oxalato) borate, and oxalato phosphates including lithium tetrafluoro (oxalato) phosphate;

and ionic compounds containing a cation of formula (II)

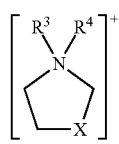

(II)

wherein
X is $CH_2$ or $NR^a$,
$R^3$ is selected from $C_1$ to $C_6$ alkyl,
$R^4$ is selected from $—(CH_2)_u—SO_3—(CH_2)_v—R^b$, $—SO_3—$ is $—O—S(O)_2—$ or $—S(O)_2—O—$, preferably $—SO_3—$ is $—O—S(O)_2—$, u is an integer from 1 to 8, preferably u is 2, 3 or 4, wherein one or more $CH_2$ groups of the $—(CH_2)_u—$ alkylene chain which are not directly bound to the N-atom and/or the $SO_3$ group may be replaced by O and wherein two adjacent $CH_2$ groups of the $—(CH_2)_u—$ alkylene chain may be replaced by a C—C double bond, preferably the $—(CH_2)_u—$ alkylene chain is not substituted and u u is an integer from 1 to 8, preferably u is 2, 3 or 4,
v is an integer from 1 to 4, preferably v is 0,
$R^a$ is selected from $C_1$ to $C_6$ alkyl,
$R^b$ is selected from $C_1$-$C_{20}$ alkyl, $C_2$-$C_{20}$ alkenyl, $C_2$-$C_{20}$ alkynyl, $C_6$-$C_{12}$ aryl, and $C_6$-$C_{24}$ aralkyl, which may contain one or more F, and wherein one or more $CH_2$ groups of alkyl, alkenyl, alkynyl and aralkyl which are not directly bound to the $SO_3$ group may be replaced by O, preferably $R^b$ is selected from $C_1$-$C_6$ alkyl, $C_2$-$C_4$ alkenyl, and $C_2$-$C_4$ alkynyl, which may contain one or more F, and wherein one or more $CH_2$ groups of alkyl, alkenyl, alkynyl and aralkyl which are not directly bound to the $SO_3$ group may be replaced by O, preferred examples of $R^b$ include methyl, ethyl, trifluoromethyl, pentafluoroethyl, n-propyl, n-butyl, n-hexyl, ethenyl, ethynyl, allyl or prop-1-yn-yl, and an anion selected from bisoxalato borate, difluoro (oxalato) borate, $[F_zB(C_mF_{2m+1})_{4-z}]^-$, $[F_yP(C_mF_{2m+1})_{6-y}]^-$, $[C_mF_{2m+1})_2P(O)O]^-$, $[C_mF_{2m+1}P(O)O_2]^{2-}$, $[O—C(O)—C_mF_{2m+1}]^-$, $[O—S(O)_2—C_mF_{2m+1}]^-$, $[N(C(O)—C_mF_{2m+1})_2]^-$, $[N(S(O)_2—C_mF_{2m+1})_2]^-$, $[N(C(O)—C_mF_{2m+1})(S(O)_2—C_mF_{2m+1})]^-$, $[N(C(O)—C_mF_{2m+1})(C(O)F)]^-$, $[N(S(O)_2—C_mF_{2m+1})(S(O)_2F)]^-$, $[N(S(O)_2F)_2]^-$, $[C(C(O)—C_mF_{2m+1})_3]^-$, $[C(S(O)_2—C_mF_{2m+1})_3]^-$, wherein m is an integer from 1 to 8, z is an integer from 1 to 4, and y is an integer from 1 to 6, Preferred anions are bisoxalato borate, difluoro (oxalato) borate, $[F_3B(CF_3)]^-$, $[F_3B(C_2F_5)]^-$, $[PF_6]^-$, $[F_3P(C_2F_5)_3]^-$, $[F_3P(C_3F_7)_3]^-$, $[F_3P(C_4F_9)_3]^-$, $[F_4P(C_2F_5)_2]^-$, $[F_4P(C_3F_7)_2]^-$, $[F_4P(C_4F_9)_2]^-$, $[F_5P(C_2F_5)]^-$, $[F_5P(C_3F_7)]^-$ or $[F_5P(C_4F_9)]^-$, $[(C_2F_5)_2P(O)O]^-$, $[(C_3F_7)_2P(O)O]^-$ or $[(C_4F_9)_2P(O)O]^-$, $[C_2F_5P(O)O_2]^{2-}$, $[C_3F_7P(O)O_2]^{2-}$, $[C_4F_9P(O)O_2]^{2-}$, $[O—C(O)CF_3]^-$, $[O—C(O)C_2F_5]^-$, $[O—C(O)C_4F_9]^-$, $[O—S(O)_2CF_3]^-$, $[O—S(O)_2C_2F_5]^-$, $[N(C(O)C_2F_5)_2]^-$, $[N(C(O)CF_3)_2]^-$, $[N(S(O)_2CF_3)_2]^-$, $[N(S(O)_2C_2F_5)_2]^-$, $[N(S(O)_2C_3F_7)_2]^-$, $[N(S(O)_2CF_3)(S(O)_2C_2F_5)]^-$, $[N(S(O)_2C_4F_9)_2]^-$, $[N(C(O)CF_3)(S(O)_2CF_3)]^-$, $[N(C(O)C_2F_5)(S(O)_2CF_3)]^-$ or $[N(C(O)CF_3)(S(O)_2C_4F_9)]^-$, $[N(C(O)CF_3)(C(O)F)]^-$, $[N(C(O)C_2F_5)(C(O)F)]^-$, $[N(C(O)C_3F_7)(C(O)F)]^-$, $[N(S(O)_2CF_3)(S(O)_2F)]^-$, $[N(S(O)_2C_2F_5)(S(O)_2F)]^-$, $[N(S(O)_2C_4F_9)(S(O)_2F)]^-$, $[C(C(O)CF_3)_3]^-$, $[C(C(O)C_2F_5)_3]^-$ or $[C(C(O)C_3F_7)_3]^-$, $[C(S(O)_2CF_3)_3]^-$, $[C(S(O)_2C_2F_5)_3]^-$, and $[C(S(O)_2C_4F_9)_3]^-$.

More preferred the anion is selected from bisoxalato borate, difluoro (oxalato) borate, $CF_3SO_3^-$, and $[PF_3(C_2F_5)_3]^-$.

The term "$C_2$-$C_{20}$ alkenyl" as used herein refers to an unsaturated straight or branched hydrocarbon group with 2 to 20 carbon atoms having one free valence. Unsaturated means that the alkenyl group contains at least one C—C double bond. $C_2$-$C_6$ alkenyl includes for example ethenyl, 1-propenyl, 2-propenyl, 1-n-butenyl, 2-n-butenyl, iso-butenyl, 1-pentenyl, 1-hexenyl, 1-heptenyl, 1-octenyl, 1-nonenyl, 1-decenyl and the like. Preferred are $C_2$-$C_{10}$ alkenyl groups, more preferred are $C_2$-$C_6$ alkenyl groups, even more preferred are $C_2$-$C_4$ alkenyl groups and in particular ethenyl and 1-propen-3-yl (allyl).

The term "$C_2$-$C_{20}$ alkynyl" as used herein refers to an unsaturated straight or branched hydrocarbon group with 2 to 20 carbon atoms having one free valence, wherein the hydrocarbon group contains at least one C—C triple bond. $C_2$-$C_6$ alkynyl includes for example ethynyl, 1-propynyl, 2-propynyl, 1-n-butinyl, 2-n-butynyl, iso-butinyl, 1-pentynyl, 1-hexynyl, -heptynyl, 1-octynyl, 1-nonynyl, 1-decynyl and the like and the like. Preferred are $C_2$-$C_{10}$ alkynyl, more preferred are $C_2$-$C_6$ alkynyl, even more preferred are $C_2$-$C_4$ alkynyl, in particular preferred are ethynyl and 1-propyn-3-yl (propargyl).

The term "$C_6$-$C_{12}$ aryl" as used herein denotes an aromatic 6- to 12-membered hydrocarbon cycle or condensed cycles having one free valence. Examples of $C_6$-$C_{12}$ aryl are phenyl and naphtyl. Preferred is phenyl.

The term "$C_7$-$C_{24}$ aralkyl" as used herein denotes an aromatic 6- to 12-membered aromatic hydrocarbon cycle or condensed aromatic cycles substituted by one or more $C_1$-$C_6$ alkyl. The $C_7$-$C_{24}$ aralkyl group contains in total 7 to 24 C-atoms and has one free valence. The free valence may be located at the aromatic cycle or at a $C_1$-$C_6$ alkyl group, i.e. $C_7$-$C_{24}$ aralkyl group may be bound via the aromatic part or via the alkyl part of the aralkyl group. Examples of $C_7$-$C_{24}$ aralkyl are methylphenyl, benzyl, 1,2-dimethylphenyl, 1,3-dimethylphenyl, 1,4-dimethylphenyl, ethylphenyl, 2-propylphenyl, and the like.

Compounds of formula (II) and their preparation are described in detail in WO 2013/026854 A1. Examples of compounds of formula (II) which are preferred according to the present invention are disclosed on page 12, line 21 to page 15, line 13 of WO 2013/026854 A1.

Preferred SEI-forming additives are oxalato borates, fluorinated ethylene carbonate and its derivatives, vinylene carbonate and its derivatives, and compounds of formula (II). More preferred are lithium bis(oxalato) borate, vinylene carbonate, monofluoro ethylene carbonate, and compounds of formula (II), in particular monofluoro ethylene carbonate, and compounds of formula (II). If the electrolyte composition contains a SEI forming additive (iv) it is usually present in a concentration of from 0.1 to 10 wt.-%, preferably of from 0.2 to 5 wt.-% of the electrolyte composition.

Examples of overcharge protection additives are compounds of formula (III)

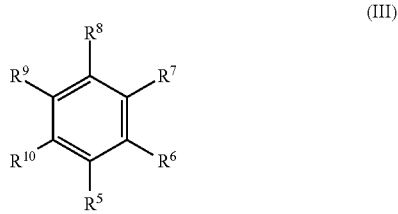

(III)

$R^5$ is cyclohexyl or $C_6$-$C_{12}$ aryl, which may be substituted by one or more substituent selected independently from each other from F, Cl, Br, I, $C_6$-$C_{12}$ aryl, and $C_1$-$C_6$ alkyl, wherein $C_6$-$C_{12}$ aryl and $C_1$-$C_6$ alkyl may be substituted by one or more substituent selected independently from each other from F, Cl, Br and I; and $R^6$, $R^7$, $R^8$, $R^9$ and $R^{10}$ may be same or different and are independently from each other selected from H, F, Cl, Br, I, $C_6$-$C_{12}$ aryl, and $C_1$-$C_6$ alkyl, wherein $C_6$-$C_{12}$ aryl and $C_1$-$C_6$ alkyl may be substituted by one or more substituent selected independently from each other from F, Cl, Br and I.

Examples of compounds of formula (III) are cyclohexylbenzene, biphenyl, o-terphenyl and p-terphenyl, preferred compounds of formula (III) are cyclohexylbenzene and biphenyl.

Examples of gelling agents are polymers like polyvinylidene fluoride, polyvinylidene-hexafluoropropylene copolymers, polyvinylidene-hexafluoropropylene-chlorotrifluoroethylene copolymers, Nafion, polyethylene oxide, polymethyl methacrylate, polyacrylonitrile, polypropylene, polystyrene, polybutadiene, polyethylene glycol, polyvinylpyrrolidone, polyaniline, polypyrrole and/or polythiophene. These polymers are added to the electrolytes in order to convert liquid electrolytes into quasi-solid or solid electrolytes and thus to improve solvent retention, especially during ageing.

A compound added as additive (iv) may have more than one effect in the electrolyte composition and the device comprising the electrolyte composition. E.g. lithium oxalato borate may be added as additive enhancing the SEI formation but it may also be added as conducting salt.

According to one embodiment of the present invention the electrolyte composition contains at least one additive (iv). Preferably the electrolyte composition contains at least one additive (iv) selected from film forming additives, flame retardants, overcharging additives, wetting agents, HF and/or $H_2O$ scavenger, stabilizer for $LiPF_6$ salt, ionic salvation enhancer, corrosion inhibitors, and gelling agents, more preferred the electrolyte composition contains at least one flame retardant additive, even more preferred the electrolyte composition contains at least one flame retardant additive selected from cyclophosphazenes, organic phosphoramides, organic phosphites, organic phosphonates, organic phosphines, and organic phosphinates, in particular preferred the electrolyte composition contains a cyclophosphazene.

In case the electrolyte composition contains one or more flame retardant additives, the electrolyte composition contains preferably in total 1 to 10 wt.-% of the one or more flame retardant additives, more preferred 2 to 5 wt.-% of the one or more flame retardant additives, based on the total weight of the electrolyte composition.

A preferred electrolyte composition contains
(i) at least 70 wt.-% of at least one organic aprotic solvent;
(ii) 0.1 to 25 wt.-% of at least one conducting salt;
(iii) 0.1 to 10 wt.-% acetic acid 2-[(methoxycarbonyl)oxy] methyl ester; and
(iv) 0 to 25 wt.-% of at least one additive,
based on the total weight of the electrolyte composition.

The water content of the inventive electrolyte composition is preferably below 100 ppm, based on the weight of the electrolyte composition, more preferred below 50 ppm, most preferred below 30 ppm. The water content may be determined by titration according to Karl Fischer, e.g. described in detail in DIN 51777 or ISO760: 1978.

The content of HF of the inventive electrolyte composition is preferably below 60 ppm, based on the weight of the electrolyte composition, more preferred below 40 ppm, most preferred below 20 ppm. The HF content may be determined by titration according to potentiometric or potentiographic titration method.

The inventive electrolyte composition is preferably liquid at working conditions; more preferred it is liquid at 1 bar and 25° C., even more preferred the electrolyte composition is liquid at 1 bar and −10° C., in particular the electrolyte composition is liquid at 1 bar and −25° C., even more preferred the electrolyte composition is liquid at 1 bar and −35° C.

The electrolyte compositions of the invention are prepared by methods which are known to the person skilled in the field of the production of electrolytes, generally by dissolving the conductive salt (ii) in the corresponding mixture of solvent(s) (i) and adding acetic acid 2-[(methoxycarbonyl)oxy] methyl ester (iii) and optionally additives (iv), as described above.

The electrolyte compositions may be used in electrochemical cells and electrooptical devices, preferred they are used electrochemical devices, more preferred in lithium batteries, even more more preferred in secondary lithium cells and most preferred in secondary lithium ion batteries.

The invention further provides an electrochemical cell or optoelectrical device comprising the electrolyte composition as described above or as described as being preferred.

The general construction of such electrochemical and electrooptical devices is known and is familiar to the person skilled in this art for batteries, for example, in Linden's Handbook of Batteries (ISBN 978-0-07-162421-3).

The electrochemical cell may be a lithium battery, a double layer capacitor, or a lithium ion capacitor.

Preferably the electrochemical or electrooptical device is a lithium battery. The term "lithium battery" as used herein means an electrochemical cell, wherein the anode comprises lithium metal or lithium ions sometime during the charge/discharge of the cell. The anode may comprise lithium metal or a lithium metal alloy, a material occluding and releasing lithium ions, or other lithium containing compounds; e.g. the lithium battery may be a lithium ion battery, a lithium/sulphur battery, or a lithium/selenium sulphur battery.

In particular preferred the electrochemical device is a lithium ion battery, i.e. a secondary lithium ion electrochemical cell comprising a cathode comprising a cathode active material that can reversibly occlude and release lithium ions and an anode comprising an anode active material that can reversibly occlude and release lithium ions. The terms "secondary lithium ion electrochemical cell" and "(secondary) lithium ion battery" are used interchangeably within the present invention.

The at least one cathode active material preferably comprises a material capable of occluding and releasing lithium ions selected from lithiated transition metal phosphates and lithium ion intercalating metal oxides.

Examples of lithiated transition metal phosphates are $LiFePO_4$ and $LiCoPO_4$, examples of lithium ion intercalating metal oxides are $LiCoO_2$, $LiNiO_2$, $LiMnO_2$, mixed transition metal oxides with layer structure having the general formula $Li_{(1+z)}[Ni_aCo_bMn_c]_{(1-z)}O_{2+e}$ wherein z is 0 to 0.3; a, b and c may be same or different and are independently 0 to 0.8 wherein a+b+c=1; and $-0.1 \leq e \leq 0.1$, and manganese-containing spinels like $LiMnO_4$ and spinels of general formula $Li_{1+t}M_{2-t}O_{4-d}$ wherein d is 0 to 0.4, t is 0 to 0.4 and M is Mn and at least one further metal selected from the group consisting of Co and Ni, and $Li_{(1+g)}[Ni_h Co_iAl_j]_{(1-g)}O_{2+k}$. Typical values for g, h, l, j and k are: g=0, h=0.8 to 0.85, i=0.15 to 0.20, j=0.02 to 0.03 and k=0.

The cathode may further comprise electrically conductive materials like electrically conductive carbon and usual components like binders. Compounds suited as electrically conductive materials and binders are known to the person skilled in the art. For example, the cathode may comprise carbon in a conductive polymorph, for example selected from graphite, carbon black, carbon nanotubes, graphene or mixtures of at least two of the aforementioned substances. In addition, the cathode may comprise one or more binders, for example one or more organic polymers like polyethylene, polyacrylonitrile, polybutadiene, polypropylene, polystyrene, polyacrylates, polyvinyl alcohol, polyisoprene and copolymers of at least two comonomers selected from ethylene, propylene, styrene, (meth)acrylonitrile and 1,3-butadiene, especially styrene-butadiene copolymers, and halogenated (co)polymers like polyvinlyidene chloride, polyvinly chloride, polyvinyl fluoride, polyvinylidene fluoride (PVdF), polytetrafluoroethylene, copolymers of tetrafluoroethylene and hexafluoropropylene, copolymers of tetrafluoroethylene and vinylidene fluoride and polyacrylnitrile.

The anode comprised within the lithium batteries of the present invention comprises an anode active material that can reversibly occlude and release lithium ions or is capable to form an alloy with lithium. For example, carbonaceous material that can reversibly occlude and release lithium ions can be used as anode active material. Carbonaceous materials suited are crystalline carbon materials such as graphite materials like natural graphite, graphitized cokes, graphitized MCMB, and graphitized MPCF; amorphous carbon such as coke, mesocarbon microbeads (MCMB) fired below 1500° C., and mesophase pitch-based carbon fiber (MPCF); hard carbon and carbonic anode active material (thermally decomposed carbon, coke, graphite) such as a carbon composite, combusted organic polymer, and carbon fiber. Some carbonaceous materials usable as anode active materials are prone to deterioration by propylene carbonate if propylene carbonate is present in the electrolyte composition. This deterioration is usually caused by intercalation of propylene carbonate molecules into the carbonaceous material during electrochemical cycling of the cell. The intercalation of the propylene molecules leads to exfoliation of layers of the carbonaceous material. For instance graphite materials are very easily destroyed by exfoliation due to intercalation of propylene carbonate. Usually carbonaceous materials comprising at least partially graphitic layers are prone to such deterioration caused by propylene carbonate present in the electrolyte composition during cycling. In order to determine whether a carbonaceous material is prone to deterioration by propylene carbonate the procedure described below may be followed:

To determine if a carbonaceous material is sensitive to deterioration caused by propylene carbonate coin button cells can be built similar to the procedure described below in the experimental section. Instead of the graphite electrode as described in the procedure the carbonaceous material based electrode is used as negative electrode. As electrolyte a solution of 1 M $LiPF_6$ in PC:DMC (1:1 by wt.) has to be used. Carbonaceous materials that are sensitive to deterioration by propylene carbonate show a strong capacity fading and have a capacity retention after 20 cycles that is below 25% based on the theoretical capacity of the cell.

The addition of acetic acid 2-[(methoxycarbonyl)oxy] methyl ester effectively prevents deterioration of carbonaceous anode active material by propylene carbonate. According to one embodiment of the invention the anode active material is selected from carbonaceous materials prone to deterioration by propylene carbonate. Preferably the anode active material is selected from carbonaceous materials comprising at least partially graphitic layers, more preferred the anode active material is selected from graphite materials.

Further anode active materials are lithium metal, or materials containing an element capable of forming an alloy with lithium. Non-limiting examples of materials containing an element capable of forming an alloy with lithium include a metal, a semimetal, or an alloy thereof. It should be understood that the term "alloy" as used herein refers to both alloys of two or more metals as well as alloys of one or more metals together with one or more semimetals. If an alloy has metallic properties as a whole, the alloy may contain a nonmetal element. In the texture of the alloy, a solid solution, a eutectic (eutectic mixture), an intermetallic compound or two or more thereof coexist. Examples of such metal or semimetal elements include, without being limited to, titanium (Ti), tin (Sn), lead (Pb), aluminum, indium (In), zinc (Zn), antimony (Sb), bismuth (Bi), gallium (Ga), germanium (Ge), arsenic (As), silver (Ag), hafnium (Hf), zirconium (Zr) yttrium (Y), and silicon (Si). Metal and semimetal elements of Group 4 or 14 in the long-form periodic table of the elements are preferable, and especially preferable are titanium, silicon and tin, in particular silicon. Examples of tin alloys include ones having, as a second constituent element other than tin, one or more elements selected from the group consisting of silicon, magnesium (Mg), nickel, copper, iron, cobalt, manganese, zinc, indium, silver, titanium (Ti), germanium, bismuth, antimony and chromium (Cr). Examples of silicon alloys include ones having, as a second constituent element other than silicon, one or more elements selected from the group consisting of tin, magnesium, nickel, copper, iron, cobalt, manganese, zinc, indium, silver, titanium, germanium, bismuth, antimony and chromium.

A further possible anode active material is silicon which is able to intercalate lithium ions. The silicon may be used in different forms, e.g. in the form of nanowires, nanotubes, nanoparticles, films, nanoporous silicon or silicon nanotubes. The silicon may be deposited on a current collector. The current collector may be a metal wire, a metal grid, a metal web, a metal sheet, a metal foil or a metal plate. Preferred the current collector is a metal foil, e.g. a copper foil. Thin films of silicon may be deposited on metal foils by any technique known to the person skilled in the art, e.g. by sputtering techniques. One possibility of preparing Si thin film electrodes are described in R. Elazari et al.; Electrochem. Comm. 2012, 14, 21-24. It is also possible to use a silicon/carbon composite as anode active material according to the present invention.

Other possible anode active materials are lithium ion intercalating oxides of Ti.

Preferably the anode active material is selected from carbonaceous material that can reversibly occlude and release lithium ions, particularly preferred the carbonaceous material that can reversibly occlude and release lithium ions is selected from carbonaceous materials prone to deterioration by propylene carbonate, in particular preferred are graphite materials. In another preferred embodiment the anode active is selected from silicon that can reversibly occlude and release lithium ions, preferably the anode comprises a thin film of silicon or a silicon/carbon composite. In a further preferred embodiment the anode active is selected from lithium ion intercalating oxides of Ti.

The anode and cathode may be made by preparing an electrode slurry composition by dispersing the electrode active material, a binder, optionally a conductive material and a thickener, if desired, in a solvent and coating the slurry composition onto a current collector. The current collector may be a metal wire, a metal grid, a metal web, a metal sheet, a metal foil or a metal plate. Preferred the current collector is a metal foil, e.g. a copper foil or aluminum foil.

The inventive lithium batteries may contain further constituents customary per se, for example separators, housings, cable connections etc. The housing may be of any shape, for example cuboidal or in the shape of a cylinder, the shape of a prism or the housing used is a metal-plastic composite film processed as a pouch. Suited separators are for example glass fiber separators and polymer-based separators like polyolefin separators.

Several inventive lithium batteries may be combined with one another, for example in series connection or in parallel connection. Series connection is preferred. The present invention further provides for the use of inventive lithium ion batteries as described above in devices, especially in mobile devices. Examples of mobile devices are vehicles, for example automobiles, bicycles, aircraft, or water vehicles such as boats or ships. Other examples of mobile devices are those which are portable, for example computers, especially laptops, telephones or electrical power tools, for example from the construction sector, especially drills, battery-driven screwdrivers or battery-driven staplers. But the inventive lithium ion batteries can also be used for stationary energy stores.

Even without further statements, it is assumed that a skilled person is able to utilize the above description in its widest extent. Consequently, the preferred embodiments and examples are to be interpreted merely as a descriptive enclosure which in no way has any limiting effect at all.

The invention is illustrated by the examples which follow, which do not, however, restrict the invention.

1. Electrolyte Compositions

Electrolyte compositions were prepared from acetic acid 2-[(methoxycarbonyl)oxy] methyl ester (GMC), ethylene carbonate (EC), propylene carbonate (PC), dimethyl carbonate (DMC), ethyl methyl carbonate (EMC), lithium hexafluorophosphate ($LiPF_6$), and vinylene carbonate (VC). The exact compositions are shown in Table 2. Wt.-% are based on the total weight of the electrolyte composition.

GMC was prepared by dissolving glycolacidmethylester in dry tetrahydrofurane and adding dry pyridine and 4-Dimethylaminopyridine (DMAP) as a base. The solution was then cooled down to 0° C. and methylchloroformiate was added slowly within 45 minutes. Afterwards the mixture was stirred at room temperature for 16 hours. The complete synthesis was carried out under inert argon atmosphere. The reaction was then quenched with deionized water and was stirred again for 15 minutes. The organic phase was separated two times extracted with hydrochloric acid (2 mol/l) and once extracted with saturated $NaHCO_3$ and afterwards two times with deionized water. Finally the organic phase was dried with sodium sulfate, filtered and reduced (35° C., 300 mbar-10 mbar). The product was then purified by distillation.

2. Electrochemical Tests

Cycling Tests:

Button cells were fabricated using lithium nickel cobalt manganese oxide ($LiNi_{0.33}Co_{0.33}Mn_{0.33}O_2$; NCM 111) electrodes with a capacity of 2 $mAh/cm^2$ and a graphite electrode (surface modified natural graphite (Hitachi Chemical, SMG-N-HE2-20), 95.7 wt % graphite, 0.5 wt % conductive additive, 3.8 wt % binder (styrene-butadiene rubber (SBR)/carboxymethylcellulose (CMC)) with a capacity of 2.15 $mAh/cm^2$. A glass-fiber filter separator (Whatmann GF/D) was used as separator, which was soaked with 100 μl of the respective electrolyte composition. All electrochemical measurements were carried out at 25° C./45° C. in climate chambers. For electrochemical testing of the cycling behavior the procedure displayed in Table 1 was used. "@4.3 V until I<0.01 C or t>30 min" means that the cell was charged at a constant voltage of 4.3 V until the electric current I was lower than 0.01 Coulomb or the charging time exceeded the time of 30 minutes. The cut-off voltage of during charging was 4.3 V, the cut-off voltage during discharging was 3.0 V.

TABLE 1

| Cycle | Charge rate in C | Constant voltage charge | Discharge rate in C | Temperature [° C.] |
|---|---|---|---|---|
| 1 | 0.1 | None | 0.1 | 25 |
| 2 | 0.2 | None | 0.2 | 25 |
| 3-6 | 0.5 | @4.3 V until I<0.01 C or t>30 min | 0.5 | 25 |
| 7 | 0.2 | @4.3 V until I<0.01 C or t>30 min | 0.2 | 25 |
| 8 | 0.2 | @4.3 V until I<0.01 C or t>30 min | 0.5 | 25 |
| 9 | 0.2 | @4.3 V until I<0.01 C or t>30 min | 1 | 25 |
| 10 | 0.2 | @4.3 V until I<0.01 C or t>30 min | 2 | 25 |
| 11 | 0.2 | @4.3 V until I<0.01 C or t>30 min | 3 | 25 |
| 12 | 0.2 | @4.3 V until I<0.01 C or t>30 min | 4 | 25 |
| 13 | 0.2 | @4.3 V until I<0.01 C or t>30 min | 5 | 25 |
| 14 | 0.2 | @4.3 V until I<0.01 C or t>30 min | 6 | 25 |
| 15-18 | 0.5 | @4.3 V until I<0.01 C or t>30 min | 0.5 | 25 |
| 19-118 | 1 | @4.3 V until I<0.01 C or t>30 min | 1 | 45 |

The results of the electrochemical cycling tests are shown in Table 2.

TABLE 2

| | Composition | 4 C discharge capacity of cycle 12 [mAh g$^{-1}$] | Capacity retention after 100 cycles based on 19th cycle [%] |
|---|---|---|---|
| Example 1 | 1M LiPF$_6$ in PC:DMC 1:1 by wt. + 1 wt.-% GMC | 106 | 88 |
| Comparative example 1 | 1M LiPF$_6$ in EC:EMC 3:7 by wt. + 2 wt.-% VC | 103 | 93 |
| Comparative example 2 | 1M LiPF$_6$ in PC:DMC 1:1 by wt. | Exfoliation, no cycling possible | |
| Comparative example 3 | 1M LiPF$_6$ in PC:DMC 1:1 by wt. + 2 wt.-% VC | Exfoliation, massive fading within 20 cycles down to 20 mAh g$^{-1}$ | |

The results of Table 2 show that acetic acid 2-[(methoxycarbonyl)oxy] methyl ester prevents effectively the exfoliation of the graphite anode by intercalation of propylene carbonate molecules. In comparison the well-known SEI forming additive vinylene carbonate has only a slight effect on the exfoliation of the graphite anode caused by the propylene carbonate. An electrochemical cell comprising graphite as anode active material and an electrolyte composition containing acetic acid 2-[(methoxycarbonyl)oxy] methyl ester and propylene carbonate shows roughly the same capacity retention after 100 cycles as a the same electrochemical cell comprising an ethylene carbonate based electrolyte composition containing vinylene carbonate as SEI forming additive.

3. Flammability and Melting Points

The flashpoints of different solvent mixtures were determined with a Grabner FLP Miniflash instrument. The starting temperature Ti was 20° C. and the final temperature Tf was 130° C. Every 1° C. ignition steps were carried out. The heating rate was 3.0° C./min. As pressure threshold value for identification of the ignition point 25 kPa were used. The flashpoints of different solvent mixtures are shown in Table 3.

| Composition | Flashpoint [° C.] |
|---|---|
| EC:DMC 1:1 by weight | 27 |
| PC:DMC 1:1 by weight | 27 |
| PC:DMC 7:3 by weight | 36 |

The melting point of different solvent mixtures is measured via DSC from low temperatures to high temperatures. The scan rate was 2 K/min and the instrument was a Netsch DSC 204. The samples were measure in sealed aluminum pans. The melting points are shown in Table 4 wherein the end of melting was taken as melting point.

TABLE 4

| Composition | Melting point [° C.] |
|---|---|
| EC:DMC 1:1 by weight | −3 |
| PC:DMC 1:1 by weight | −26 |

The results displayed in Tables 3 and 4 show that compositions comprising mixtures of PC instead of EC and DMC at the same concentration have same flash points but the PC comprising solvent mixture has a considerably lower melting point and can therefore be used as solvent mixture for low temperature electrolyte compositions without decreasing the flammability.

The invention claimed is:

1. An electrolyte composition comprising:
   (i) at least one aprotic organic solvent which includes at least about 50 wt.-% propylene carbonate;
   (ii) at least one conducting salt;
   (iii) between about 0.1 wt.-% and about 10 wt.-% of acetic acid 2-[(methoxycarbonyl)oxy] methyl ester (iii) based on the total weight of the electrolyte composition; and
   (iv) optionally one or more additives.

2. The electrolyte composition according to claim 1, wherein the electrolyte composition comprises 0.5 to 2 wt.-% of the acetic acid 2-[(methoxycarbonyl)oxy] methyl ester (iii) based on the total weight of the electrolyte composition.

3. The electrolyte composition according to claim 1, wherein at least one conducting salt (ii) is selected from the group consisting of lithium salts.

4. The electrolyte composition according to claim 1, wherein the electrolyte composition comprises at least one additive (iv) selected from the group consisting of film forming additives, flame retardants, overcharging additives, wetting agents, HF and/or H$_2$O scavenger, stabilizer for LiPF$_6$ salt, ionic salvation enhancer, corrosion inhibitors, and gelling agents.

5. The electrolyte composition according to claim 1, wherein the electrolyte composition comprises at least one flame retardant additive selected from the group consisting of cyclophosphazenes, organic phosphoramides, organic phosphites, organic phosphates, organic phosphonates, organic phosphines, and organic phosphinates.

6. The electrolyte composition according to claim 1, wherein the electrolyte composition comprises in total 1 to 10 wt.-% of one or more flame retardant additives.

7. The electrolyte composition according to claim 1, wherein the electrolyte composition comprises:
   (i) at least 70 wt.-% of at least one aprotic organic solvent which includes at least about 50 wt.-% propylene carbonate;
   (ii) 0.1 to 25 wt.-% of the at least one conducting salt;
   (iii) 0.1 to 10 wt.-% of the acetic acid 2-[(methoxycarbonyl)oxy] methyl ester; and
   (iv) 0 to 25 wt.-% of the at least one additive,
   based on the total weight of the electrolyte composition.

8. An electrochemical cell comprising the electrolyte composition according to claim 1.

9. The electrochemical cell according to claim 8, wherein the electrochemical cell is a lithium battery.

10. The electrochemical cell according to claim 8, wherein the electrochemical cell comprises an anode comprising an anode active material selected from the group consisting of carbonaceous materials prone to deterioration by propylene carbonate.

* * * * *